US005762931A

United States Patent [19]

Talwar et al.

[11] Patent Number: 5,762,931
[45] Date of Patent: Jun. 9, 1998

[54] ANTI-CANCER UTILITY OF HCG VACCINES

[75] Inventors: Gursaran P. Talwar, New Delhi, India; Debajit K. Biswas, Boston, Mass.

[73] Assignee: National Institute of Immunology, New Delhi, India

[21] Appl. No.: 295,774

[22] PCT Filed: Dec. 31, 1992

[86] PCT No.: PCT/US92/11333

§ 371 Date: Nov. 7, 1994

§ 102(e) Date: Nov. 7, 1994

[87] PCT Pub. No.: WO94/15633

PCT Pub. Date: Jul. 21, 1994

[51] Int. Cl.⁶ .......................... A61K 38/18; A61K 39/00; A61K 39/395; C07K 16/00
[52] U.S. Cl. ......................... 424/138.1; 424/198.1; 424/145.1; 424/158.1; 424/174.1; 530/399; 530/388.24
[58] Field of Search ............................. 424/138.1, 198.1, 424/145.1, 158.1, 174.1; 530/399, 388.24

[56] References Cited

U.S. PATENT DOCUMENTS

| | | |
|---|---|---|
| 4,161,519 | 7/1979 | Talwar . |
| 4,767,842 | 8/1988 | Stevens . |
| 4,780,312 | 10/1988 | Talwar . |
| 5,006,334 | 4/1991 | Stevens . |

FOREIGN PATENT DOCUMENTS

| | | |
|---|---|---|
| WO 86/07383 | 12/1986 | WIPO . |
| WO 91/05049 | 4/1991 | WIPO . |

OTHER PUBLICATIONS

Rivera, et al., Loss of Tumorigenic Potential by Human Lung Tumor Cells in the Presence of Antisense RNA Specific to the Ectopically Synthesized Alpha Subunit of Human Chorionic Gonnadotropin *The Journal of Cell Biology*, vol. 108 2423–2334 (1989).

Wiktor et al., "Protection from Rabies by a Vaccina Virus Recombinant Containing the Rabies Virus Glycoprotein Gene" *Proc. Natl. Acad. Sci. USA* 81:7194–7198 (1984).

*Primary Examiner*—Lila Feisee
*Assistant Examiner*—Geetha P. Bansal
*Attorney, Agent, or Firm*—Morrison & Foerster LLP

[57] ABSTRACT

This invention relates to a method of combatting cancer which cancer releases chorionic gonadotropin or a subunit thereof present in a mammal which method comprises administering to said animal an anti-cancer effective amount of a birth-control vaccine or an antibody to said chorionic gonadotropin or subunit thereof. Birth-control vaccines which are polyvalent vaccines and birth-control vaccines which employ recombinant organisms incorporating sequences coding for reproductive hormones are of particular interest as well as polyclonal and monoclonal antibodies to the chorionic gonadotropin.

13 Claims, No Drawings

ANTI-CANCER UTILITY OF HCG VACCINES

BACKGROUND OF THE INVENTION

Human chorionic gonadotropin (hCG) is normally made by the trophoblast as an early hormonal signal of pregnancy. Its inactivation by bio-effective antibodies leads to the prevention of pregnancy. One of us, Talwar, has been involved in the development of two types of birth control vaccines, which induce the formation of antibodies competent to inactivate the bioactivity of hCG and thus control fertility. We have now found an additional use of such vaccines and the antibodies generated by them in prevention and cure of cancers secreting hCG. hCG and/or its $\alpha$ or $\beta$ subunits are observed to be made by a number of cancers as ectopic products. Our recent studies on one is such cancer, e.g. the human lung cancer, demonstrate that hCG and/or its subunits made by the human lung cancer cells act as autocrine growth promoters for the tumour cells. Furthermore, antibodies inactivating the hormone or its subunits arrest the growth of tumour cells in soft agar as also on progression of implanted tumour in nude mice in vivo. In cases in which antibodies are given to the animal prior to the implantation of the human lung cancer, the tumour fails to grow. The effect is dose dependent. When the antibodies are given to nude mice in which the tumour has previously grown, the antibodies cause necrosis of the tumour. These examples demonstrate the utility of the antibodies and/or the vaccines generating such antibodies, to cure as well as prevent hCG secreting tumours.

The birth control vaccine may, for example, be a vaccine of the type disclosed in U.S. Pat. No. 4,780,312 issued 25 Oct. 1988 (inventor: G. P. Talwar). Another type of birth-control vaccine with this utility as an anti-cancer agent is a recombinant birth-control vaccine of the type disclosed in WO 91/05049 (inventors: G. P. Talwar et al).

Rivera et al in J. Cell Biol. 108: 2423–2434 (1989) showed that a clonal strain of human lung tumour cells which secrete large amounts of alpha and lower levels of beta subunits of human chorionic gonadotropin (hCG) in culture lose characteristics associated with tumorigenic potential (anchorage-independent growth) when in the presence of anti-alpha-hCG antibody. This effect could be partially reversed by adding alpha-hCG to the medium.

The work of Rivera et al (op. cit.) shows that there is a need to develop a vaccine which is compatible with the immune system of a tumour-containing animal and indeed induces the immune system of the animal to produce antibodies to the tumour.

Various Ohio State University patents to Stevens (e.g. U.S. Pat. No. 4,767,842) disclose the use of a beta-hCG/tetanus toxoid modified peptide (as described in U.S. Pat. No. 4,161,519 to Talwar) as an anti-cancer agent. In U.S. Pat. No. 4,767,842 examples XXXIV and XXXVI to XXX-VIII relate to this utility. Some or all of the same examples are also disclosed in other patents related to U.S. Pat. No. 4,767,842. In all Stevens' examples the animals were immunized before exposure to cancer cells and therefore relate to the use of such antigens in the prevention rather than the cure of cancer. Stevens does not show the use of such an antigen in the cure of an already existing cancer.

Talwar (U.S. Pat. No. 4,780,312) and Talwar et al (WO 91/05049) have worked to present a reproductive hormone to the immune system of a female mammal in such a way that the immune system of the female mammal is stimulated to produce antibodies to the reproductive hormone thereby disrupting conception and providing a means of birth control. In a collaborative work from Dr. Biswas's laboratory and Dr. Talwar's laboratory it has been reported that human lung cancer cells in culture which produce the alpha subunit of hCG induced tumours in female athymic mice. These tumours in athymic mice undergo necrotic degeneration following local or intraperitoneal administration of an alpha specific antibody. The alpha hCG specific antibody did not affect the growth of tumours produced by human tumour cells which do not produce alpha-hCG. It is also demonstrated that withdrawal of the antibody treatment led to the regeneration of tumours.

These observations predict that active production of anti-tumorigenic specific antibodies such as alpha hCG in the tumour-bearing animals as a result of active stimulation by a vaccine, specifically a birth-control vaccine of the type discussed above. This overcomes the problem of renewed tumorigenesis when antibody treatment is discontinued and also problems which may arise, when antibody treatment is employed, of antibodies to the treatment antibodies being produced. The invention is especially useful in controlling cancers which are dependent for their growth and expansion on such molecules as reproductive hormones which the cancer itself often produces. By means of the invention a positive feed-back loop which promotes cancer growth can be interrupted.

SUMMARY OF THE INVENTION

In one aspect this invention provides a method of combatting a cancer in a male or female mammal which cancer releases chorionic gonadotropin or a subunit thereof which method comprises administering to said mammal an anti-cancer effective amount of an antibody a birth-control vaccine to said chorionic gonadotropin or subunit thereof.

In another aspect this invention provides a commercial package comprising an anti-cancer effective amount of a birth-control vaccine or antibody to chorionic gonadotropin or subunit thereof together with instructions for use of said birth-control vaccine or antibody as an anti-cancer agent in a male or female mammal.

The following are various preferred features of the invention.

In a preferred embodiment the vaccine or antibody is administered to a mammal which already has cancer (this is curative rather than preventative).

In methods and uses of the invention if an antibody is used in passive immunization, the antibody may be monoclonal or polyclonal. In a preferred embodiment the antibody is an anti-alpha-hCG antibody.

In methods and uses of the invention the cancer releases a first peptide of a reproductive hormone and in "active" immunization the vaccine induces antibody production, said antibody specifically binding to said peptide. In a further preferred feature the peptide is selected from alpha and beta subunits of chorionic gonadotropin. The peptide of the reproductive hormones is preferably a peptide of a human reproductive hormone.

The vaccine can be monovalent or polyvalent. When polyvalent preferably the vaccine comprises at least two hormone antigens of the reproductive system at least one of which is chorionic gonadotropin or a subunit thereof and at least one subject-compatible carrier, said polyvalent vaccine being selected from the group consisting of: (i) a composite conjugate of at least two separate antigens linked to the same carrier moiety, (ii) a mixture of conjugates of at least two separate antigens each separately linked to at least one carrier, (iii) an annealed composite of at least two separate antigens which are β subunit of hCG and an β subunit of hCG; conjugated to a carrier, and (iv) a mixture of at least two of (i) to (iii).

Alternatively the polyvalent vaccine comprises at least two antigens of the reproductive system, a first being from a preparation of a β subunit of hCG and a second being a preparation of an α subunit of hCG and at least one subject-compatible carrier, said polyvalent vaccine being selected from the group consisting of: (i) a composite conjugate of at least two separate antigens linked to the same carrier moiety, (ii) a mixture of conjugates of at least two separate antigens each separately linked to at least one carrier, (iii) an annealed composite of at least two separate antigens which are a β subunit of hCG and an α subunit of hCG; conjugated to a carrier, and (iv) a mixture of at least two of (i) to (iii).

In particularly preferred embodiments more than one (especially two) subject-compatible carrier is present. Also preferably at least two separate antigens are hormonal subunits (e.g. alpha or beta-human chorionic gonadotropin).

The subject compatible carrier preferably is one or more members selected from the group consisting of tetanus toxoid, cholera toxin B-chain, hepatitis B surface protein, a malarial protein, diphtheria toxoid and sporozoite coat protein of P. falciparum. Especially preferred are tetanus toxoid or cholera toxin B-chain.

The polyvalent vaccine may be mixed with an adjuvant selected from the group consisting of alum, detoxified sodium phthalyl derivative of salmonella lipopolysaccharide (SPLPS) and 6-o-dipalmitoyl-glycerylsuccinyl (MDP).

In another embodiment the birth-control vaccine comprises a recombinant virus incorporating in a non-essential part of the virus genome a heterologous nucleotide sequence capable of expressing a peptide of a chorionic gonadotropin or an immunologically stimulatory fragment thereof which peptide or fragment thereof has an epitope in common with said gonadotropin released by said cancer.

In a preferred feature a first sequence codes for a chorionic gonadotropin or active fragment thereof in reading frame alignment with a second sequence coding for at least part of a transmembrane anchor sequence of a Vesicular Stomatitis Virus Glycoprotein gene.

In a further preferred feature the nucleotide sequence comprises a first sequence coding for a chorionic gonadotropin or active fragment thereof in reading frame alignment with a second sequence coding for at least part of a transmembrane anchor sequence of a Rabies Glycoprotein gene.

Alternatively the nucleotide sequence codes for (A) a fused peptide comprising a first sequence coding for an alpha or beta subunit of a mammalian gonadotropin in reading frame alignment with a second sequence coding for a peptide anchor sequence whereby said nucleotide sequence, when inserted into a virus, said virus subsequently used to infect a host cell and the fused peptide subsequently expressed, said fused peptide is anchored to the host cell membrane, or (B) an alpha subunit of a mammalian gonadotropin inserted into a viral nucleotide sequence, said alpha subunit of said mammalian gonadotropin being capable of annealing to said membrane anchored peptide on co-expression of said alpha subunit of said mammalian gonadotropin along with the membrane anchored peptide in the same host cell.

Such a nucleotide sequence (A) may comprise a first sequence coding for an alpha subunit of chorionic gonadotropin, or a beta subunit of chorionic gonadotropin in reading frame alignment with a second sequence coding for at least part of a Vesicular Stomatitis Virus Glycoprotein gene.

Alternatively such a nucleotide sequence (A) may comprise a first sequence coding for an alpha subunit of human chorionic gonadotropin, or a beta subunit of human chorionic gonadotropin in reading frame alignment with a second sequence coding for a gene or gene fragment of a hepatitis B surface protein, or coding for at least part of a Vesicular Stomatitis Virus Glycoprotein gene. The second sequence may code for a transmembrane peptide or protein of at least part of a Vesicular Stomatitis Virus Glycoprotein gene.

In another preferred embodiment of the recombinant virus the first sequence comprises the beta unit of human chorionic gonadotropin in reading frame alignment with a gene coding for the middle protein of a hepatitis B surface protein. An especially preferred embodiment of such a recombinant virus is designated vSS4.

In another embodiment the birth-control vaccine comprises a recombinant virus including nucleotide sequence (B) comprising an alpha subunit of a mammalian gonadotropin inserted into a viral nucleotide sequence, said alpha subunit of said mammalian gonadotropin being capable of annealing to said membrane anchored peptide on co-expression of said alpha subunit of said mammalian gonadotropin along with the membrane anchored peptide in the same cell.

In a further embodiment the birth control vaccine additionally is capable of raising an antibody to at least one protein or peptide unassociated with the mammalian reproductive system. The protein or peptide unassociated with the mammalian reproductive system may be a hepatitis B surface protein or fragment thereof.

In a further embodiment the virus comprises a recombinant avipox virus incorporating a heterologous gene sequence coding for a human chorionic gonadotropin or active fragment thereof. The heterologous sequence may code, for example, for the alpha unit of human chorionic gonadotropin.

In another embodiment the virus comprises a recombinant avian poxvirus comprising a nucleotide sequence coding for a chorionic gonadotropin peptide in reading frame alignment with an avian poxvirus nucleotide, said recombinant poxvirus being capable of expressing said peptide and stimulating an antibody response thereto when a mammal is inoculated with said recombinant poxvirus.

In a preferred embodiment the cancer generates a peptide of a reproductive hormone and said vaccine comprises a recombinant virus incorporating a heterologous gene sequence coding for said peptide of said reproductive hormone or an active fragment thereof.

DESCRIPTION OF THE INVENTION

Epidemiological surveys indicate that human lung cancers are often associated with ectopic synthesis of hormones, predominantly human chorionic gonadotropin (hCG). Increased circulating levels of hCG and its subunits are often used as biochemical markers for malignancy, and decreased levels of the hormone hCG are often used as markers for successful surgery in human lung tumours. Under physiological conditions, hCG is synthesized during the early stages of pregnancy by trophoblastic cells. The ectopic synthesis of the hormone by lung tumours is an inappropriate expression.

The role of ectopic synthesis of the alpha subunit of hCG in the transformation process in a cultured cell line (ChaGo) has been examined (a list of hCG-producing lung tumour cell lines is included in Table 1 by way of example and Table 2 lists references to ectopic hormone production by tumours of human tissues). This cell line was derived from a human bronchiogenic squamous cell carcinoma (See Fashhan et al, Proc. Natl. Acad. Sci. USA 70: 1419–1422 (1973) and Rivera et al, op. cite). ChaGo cells synthesize and secrete both the alpha and beta subunits of hCG. The clonal strain of ChaGo cells used by way of example produces predominantly large amounts of alpha hCG. Rivera et al (op. cit.), in addition to reporting the anti-tumorigenic effect of anti-alpha-hCG antibody, also found that stimulation of a alpha-hCG synthesis by cyclic adenosine monophosphate in the ChaGo cells also stimulated cell proliferation and cell progression into the S phase. The results below confirm that alpha hCG acts as an autocrine growth factor and plays an important role in the transformation by maintaining the cells in a constantly proliferating state. Vaccines inducing the formation of anti-hCG antibodies have been developed (Talwar and Talwar et al (op. cit.) and Talwar et al Proc. Natl. Acad. Sci. USA 73: 218–222 (1976) and are now undergoing phase I and phase II clinical trials as birth control vaccines (Talwar et al Contraception 41: 301–316 (1990)). A similar therapeutic approach to birth control for treatment of cancers which show ectopic synthesis of such hormones is therefore now feasible.

Materials and Methods

Tissue Culture

ChaGo cells were grown in Ham's F-10 medium (GIBCO Laboratories, Grand Island, N.Y.) supplemented with 10% fetal bovine serum at 370° C. in 95% air and 5% $CO_2$. The details of the soft-agar technique were described in Rivera et al (op. cit.).

Anti-α-hCG Antibody

The α subunit of the human chorionic gonadotropin (α-hCG), at 100 μg/mL in saline, was mixed with equal amounts of complete Freund adjuvant, and 2 mL of this mixture was administered intradermally to goats. The purity of the αhCG samples used for raising the antibody was verified by sodium dodecyl sulfate-polyacrylamide gel electrophoresis. A single protein band was observed with electrophoretic mobility comparable to that of the authentic α-hCG obtained from the Hormone Distribution Agency (National Institutes of Health, Bethesda, Md.). Booster injections, with the same amount of antigen in incomplete Freund adjuvant, were given three times every 30 days after the primary injection. Animals were then rested for 6 months and given booster injections again with the same amount of antigen in incomplete Freund adjuvant. These goats were bled after 12 days, and the antigen-binding capacity of the serum was titrated by radioimmunoassay.

The specific batch of polyvalent antibodies used in this investigation has the antigen-binding capacity of 1892 μg/mL. The serum was diluted with phosphate-buffered saline to obtain the desired concentrations for administration to athymic mice. Control serum was obtained from the same goat prior to immunization. This normal goat serum was also diluted to the same degree and administered to the control animals.

Rivera et al (op. cit.) reported the inhibition of growth of ChaGo cells in tissue culture and soft agar in the presence of anti-alpha-hCG antibody. These properties were confirmed in our new batch of antibody.

Tumour Induction in Athymic Mice

Female athymic mice (nu/nu mice, 3–4 weeks old) were obtained from the National Cancer Institute Frederick Cancer Research and Development Center (Frederick, Md.). These animals were housed in sterile cages, maintained on sterile food and water, and separated from other animals. Tumours were induced by the implantation of $1-2\times10^6$ ChaGo cells under the dorsal skin of the mice. The animals were examined routinely for palpable tumour growth. Tumour growth was monitored by routine photography. Tumours were induced in 95% of the animals in a predicted time sequence by one implantation of the indicated number of ChaGo cells.

Histology

Tumours at different stages of development were surgically removed from treated and control animals and a small fragment of each tumour was fixed in 10% formalin. Paraffin sections of these tumour fragments were stained with hematoxylin and eosin, after which they were examined and photographed under a phase-contract microscope at the magnifications indicated in the legends to the figures.

Induction of Necrosis of ChaGo Cell-Induced Tumour in Athymic Mice by Anti-α-hCG The influence of local administration of the anti-alpha-hCG antibody on the growth of the ChaGo cell-induced ($1\times106$) tumours was examined. Two weeks after ChaGo cells were implanted, the tumour attained a workable size. At that time 500 ng of anti-alpha-hCG antibody was administered to five experimental animals on the same site, twice a week, under the tumour. Two control animals routinely received equivalent amounts of normal goat serum (0.5 ml). Growth of the tumours was then monitored and photographed 2, 3 and 5 weeks after the first administration of anti-alpha-hCG antibody-containing serum or the normal goat serum. The experiment was repeated three times with the same number of control and treatment animals (making a total of 6 and 15 animals respectively). All animals showed similar patterns of tumour growth in the control groups and the same degree of tumour necrosis in the treated groups.

When the anti-α-hCG antibody treatment was stopped, the genesis process resumed in all three experimental animals. In the absence of the specific antibody, the residual cells proliferated, and the tumour-mass progressively regenerated from the residual tumour cells within 4 weeks after the antibody treatment was discontinued. These results demonstrate that tumour necrosis was specifically induced by the α-hCG antibody in the administered serum. The tumour cells were deprived of the autocrine growth factor alpha-hCG, presumably due to the formation of the complex with antibody. Depriving the cells of alpha-hCG not only inhibited tumour growth but also induced extensive tumour necrosis.

The process of active necrosis in the presence of anti-α-hCG antibody was more evident from the histopathological examination of the treated tumour tissue. The results demonstrated that the untreated tumour cells were proliferating with high mitotic index. However, the histopathology of the treated tumour showed increased cellular necrosis with longer treatment with the alpha-hCG antibody. After 5 weeks of anti-alpha-hCG antibody treatment, patches of tumour cells were surrounded by massive necrotic tissue. Pinocytosis and extensive tumour cell damage were observed. These results demonstrate regression of ChaGo cell-induced tumours by the local administration of anti-alpha-hCG antibody, presumably because the cells were deprived of the essential growth factor produced by the cells themselves.

Inhibition of Growth of ChaGo Cell-Induced Tumour by Simultaneous Administration of Anti-α-hCG Antibody The results above show necrosis of tumour cells and regression of tumours by alpha-hCG antibody treatment. The results presented in this section demonstrate a concentration-dependent inhibition of tumour growth and tumour induction in athymic mice in the presence of antialpha-hCG antibody. The same number of ChaGo cells ($1\times10^6$) suspended in 0.5 mL of phosphate-buffered saline containing 50–500 ng of anti-alpha-hCG antibody were transplanted under the dorsal skin of athymic mice (three animals in each treatment group). The control animals (three animals) also received the same number of cells with equivalent amounts of normal goat serum. The antibody treatment was continued at the respective concentrations, administered twice a week locally at the site of tumour cell transplantation.

The results show the pattern of tumour growth in the absence and in the presence of indicated amounts of antibody as recorded by photography at different intervals (2 weeks after tumour cell transplantation, 4 weeks, 6 weeks, 8 weeks, and 10 weeks). Tumours grew in the control animals in an unrestricted manner and attained the indicated size within 8 weeks. Histo-pathological examination of sections of the ChaGo cell-induced tumours showed cell proliferation with a high mitotic index. No visible necrosis of the tumour cells was detected. Although the continued treatment with 50 and 100 ng of anti-alpha-hCG antibody did not substantially inhibit tumour growth, necrosis of tumour tissue was evident. Treatment with 200 ng of anti-alpha-hCG antibody, on the other hand, significantly inhibited tumour growth. At 500 ng there was no palpable growth, even 10 weeks after transplantation of the tumour cells in the presence of continuous antibody treatment.

Histopathological examination of tumour tissues treated with 500 ng of anti-alpha-hCG antibody revealed partial necrosis. These results demonstrate that tumour growth can be inhibited and completely prevented by depriving the cells of alpha-hCG by continuous exogenous administration of the antibody. A similar pattern of tumour growth inhibition was observed following intraperitoneal administration of anti-alpha-hCG antibody simultaneously with the transplantation of ChaGo cells at the dorsal surface of the animals. Continued passive immunization twice a week with 500 and 1000 ng of anti-alpha-hCG antibody prevented tumour growth completely.

The specificity of the anti-alpha-hCG antibody effect on the ChaGo cell-induced tumour was verified by examining the effect of anti-alpha-hCG on the growth of tumours induced by two hCG-nonproducing human tumour cells in culture. Human cell lines A431 (epidermoid carcinoma) and T24 (bladder carcinoma) induced tumours in athymic mice, but the growth of both of these two types of tumours was not affected by anti-alpha-hCG antibody treatment.

These results support a role for alpha-hCG in the in vivo genesis of a hormone-producing human lung tumour. They also demonstrate a reversal of tumour phenotypes by the specific antibody. The fact that the tumour growth inhibition and prevention were observed only with the anti-aloha-hCG antibody-containing serum, and not with the serum obtained from the same goat prior to immunization, strongly suggests that this effect is due to the specific antibody and not to some other agents in the serum. The two sera are isotypically matched, except that the one obtained after immunization contained the specific antibody.

The results of the experiments on treatment withdrawal further substantiate the specificity of the effect of administered anti-alpha-hCG antibody. Removal of the anti-alpha-hCG antibody reversed the tumour growth inhibitory effect, even in the presence of normal goat serum. In the absence of the anti-alpha-hCG antibody the tumour grew back.

The results obtained provide a basis for the therapeutic treatment of hormone-producing cancers by use of vaccines against the hormones produced by the cancers. External monitoring of the progression or regression of the cancer can be used to adjust dosage and use frequency to ensure control and, preferably, elimination of the cancer.

In administering such birth-control vaccines for the purpose of controlling cancer it is suggested that the initial dose and frequency be similar to that used for birth-control purposes in female mammals. Frequency and dose can then be adjusted afterwards according to the response of the cancer and the comfort of the patient. As survival rather than reproductive status of the patient is important dose and dose frequency can be adjusted accordingly.

In U.S. Pat. No. 4,780,312 200–300 g rats were inoculated with 10 µg of conjugated gonadotropin and bonnet monkeys inoculated with 50 µg of conjugated LH. Dose ranges may be 0.1 µg to 1000 µg per kg body weight, preferably 1 µg to 100 µg per kg body weight, particularly about 3 to 70 µg per kg body weight.

In the case of recombinant virus vaccines doses of such virus which would lead to similar concentrations of conjugated birth-control hormone are suggested. The required dose will, of course, vary widely from virus to virus and has to be determined empirically.

The use of vaccines is an "active" immunization approach which induce the formation of antibodies in the body of the recipient. Dose, therefore, is related to the ability of the dose to raise antibodies.

The use of antibodies is a "passive" immunization approach. The dose of such antibodies depends upon tumour load.

TABLE 1

| Name | HCG Production | Source & Reference |
|---|---|---|
| A. Squamous Cell Carcinoma ||||
| 1. ChaGo C1 | aHCG and bHCG | Tashjian | (8) |
| 2. ChaGo C5* | aHCG and bHCG | Tashjian | (8) |
| 3. ChaGo C10 | bHCG and aHCG | Tashjian | (8) |
| 4. ChaGo K1 | aHCG | ATCC | (8) |
| 5. EPLC-32M1 | aHCG | Gazdar | (4) |
| 6. EPLC-65H | aHCG and bHCG | Gazdar | (4) |
| 7. NCI-H520 | aHCG and bHCG | ATCC | (4) |
| 8. U1752 | bHCG | Gazdar | (4) |
| 9. A549 | aHCG and bHCG | ATCC | (4) |
| B. Adenocarcinoma ||||
| 10. NCI-H23 | aHCG and bHCG | Gazdar | (4) |
| 11. NCI-H358 | aHCG and bHCG | Gazdar | (4) |
| 12. NCI-H650 | aHCG and bHCG | Gazdar | (4) |
| 13. NCI-H752 | aHCG | Gazdar | (4) |
| 14. NCI-H820 | aHCG | Gazdar | (4) |
| C. Large Cell Carcinoma ||||
| 15. LCLC-103H | aHCG and bHCG | Gazdar | (4) |
| D. Adenosquamous Carcinoma ||||
| 16. NCI-H125 | bHCG | Gazdar | (4) |
| 17. NCI-H596 | aHCG | ATCC | (4) |
| E. Non-Small-Cell Carcinoma with Neuroendocrine Markers ||||
| 18. NCI-H460 | aHCG | ATCC | (4) |
| 19. NCI-H810 | bHCG | Gazdar | (4) |
| F. Small-Cell Carcinoma ||||
| 20. NCI-H679 | aHCG and bHCG | Gazdar | (4) |
| 21. NCI-H720 | bHCG | Gazdar | (4) |
| 22. NCI-H727 | aHCG and bHCG | Gazdar | (4) |
| 23. SCLC-16HC | aHCG | Gazdar | (4) |
| 24. NCI-H678 | bHCG | Gazdar | (4) |
| 25. NCI-H841 | aHCG and bHCG | Gazdar | (4) |
| 26. DMS-79 | aHCG | Gazdar | (4) |
| G. Extrapulmonary Small-Cell Carcinoma ||||
| 27. NCI-H510 | aHCG | Gazdar | (4) |

*Our preliminary observations are made from the experiments with this cell line.

TABLE 2

Ectopic Hormone Production by Tumors of Human Tissues

| Ectopic Hormone | Tumor Tissues | References |
| --- | --- | --- |
| HCG | Lung | Tashjian et al., 1973 |
| HCG | Lung | Barrial & Zapata, 1982 |
| HCG | Lung | Dempo et al., 1981 |
| HCG | Lung | Wilson et al., 1981 |
| HCG | Lung | Tanimura, 1985 |
| HCG | Lung | Hyderman, 1985 |
| HCG | Bladder | Shah et al., 1986 |
| HCG | Sweat gland of vulva | Fukuma et al., 1986 |
| HCG | Testes | Jibiki et al., 1985 |
| HCG | Breast | Lee et al., 1985 |
| HCG | Epidermis | Nagelberg et al., 1985 |
| HCG | Testes | Bates & Longo, 1985 |
| HCG | Bladder | Rodenburg et al., 1985 |
| HCG | Gastric mucosa | Manabe et al., 1985 |
| HCG | Bladder | Yamase et al., 1985 |
| HCG | Hydatiform mole | Romero et al., 1985 |
| HCG | Testes | Tseng et al., 1985 |
| HCG | Testes | Moriyama et al., 1985 |
| HCG | Gastric mucosa | Yonemura et al., 1985 |
| HCG | Hydatiform mole | Imamichi, 1985 |
| HCG | Gastric mucosa | Ohyama et al., 1985 |
| HCG | Genital tract | Norman et al., 1985 |
| HCG | Genital tract | Bhattacharya, 1985 |
| HCG | Liver | Nakagawara et al., 1985 |
| HCG | Colon | Hainsworth et al., 1985 |
| HCG | Testes | Hustin et al., 1985 |
| HCG | Testes | Boewer et al., 1985 |
| HCG | Colon | Metz et al., 1985 |
| HCG | Adrenal gland | Maeyama et al., 1985 |
| HCG | Epidermis | Nagelberg et al., 1985 |
| HCG | Thyroid | Wurzel et al., 1984 |
| HCG | Ovary | Kapp et al., 1985 |
| HCG | Testes | de Bruijin et al., 1985 |
| HCG | Testes | Alm et al., 1984 |
| HCG | Uterus | Mukher et al., 1984 |
| HCG | Ovary | Brunstein et al., 1978 |
| ACTH | Thymus | Lowry et al., 1976 |
| ACTH | Liver | Himsworth et al., 1977 |
| ACTH | Lung | Bertanga et al., 1978 |
| ACTH | Lung | Holander et al., 1982 |
| ACTH | Lung | Davis & Mary, 1982 |
| AFP | Testes | Jibiki et al., 1985 |
| AFP | Testes | Bates & Longo, 1985 |
| AFP | Liver | Nakawara et al., 1985 |
| hPL | Breast | Sheth et al., 1977 |
| PTH | Epidermis | Minne et al., 1978 |
| hGH | Ovary, Breast & Long | Kagaowicz et al., 1979 |

We claim:

1. A method of treating a tumor in a mammal, cells of which tumor release a polypeptide selected from the group consisting of chorionic gonadotropin and a subunit thereof comprising: administering to said mammal having said tumor an effective amount of anti-alpha-hCG antibody or a birth-control vaccine comprising an alpha subunit of chorionic gonadotropin to induce necrosis of tumor cells and thereby regression of said tumor.

2. A method according to claim 1 wherein said vaccine further comprises a beta subunit of chorionic gonadotropin.

3. A method according to claim 2 wherein said chorionic gonadotropin is a human chorionic gonadotropin.

4. A method according to claim 1 wherein said vaccine is monovalent.

5. A method according to claim 1 wherein said vaccine is polyvalent.

6. A method according to claim 5 wherein said polyvalent vaccine comprises at least two hormone antigens of the reproductive system one of which said hormone antigens is said alpha subunit of chorionic gonadotropin and at least one subject-compatible carrier, said polyvalent vaccine being selected from the group consisting of:

(i) a composite conjugate of at least two separate hormone antigens linked to the same carrier moiety, (ii) a mixture of conjugates of at least two separate hormone antigens each separately linked to at least one carrier, (iii) an annealed composite of at least two separate hormone antigens one of which is said alpha subunit of chorionic gonadotropin and the second of which is a beta subunit of chorionic gonadotropin, conjugated to a carrier, and (iv) a mixture of at least two of (i) to (iii).

7. A method according to claim 5 wherein said polyvalent vaccine comprises at least two hormone antigens of the reproductive system, the first being beta subunit of chorionic gonadotropin and the second being said alpha subunit of chorionic gonadotropin and at least one subject-compatible carrier, said polyvalent vaccine being selected from the group consisting of:

(i) a composite conjugate of at least two separate of the said two hormone antigens linked to the same carrier moiety, (ii) a mixture of conjugates of at least two separate of the said two hormone antigens each separately linked to at least one carrier, (iii) an annealed composite of at least two of the said separate hormone antigens conjugated to a carrier, and (iv) a mixture of at least two of (i) to (iii).

8. A method according to claim 6 wherein in said polyvalent vaccine more than one subject-compatible carrier is present.

9. A method according to claim 6 wherein in said polyvalent vaccine both of the two separate antigens are hormonal subunits.

10. A method according to claim 6 wherein in said polyvalent vaccine two subject-compatible carriers are present.

11. A method according to claim 6 wherein in said polyvalent vaccine said subject compatible carrier is one or more members selected from the group consisting of tetanus toxoid, cholera toxin B-chain, hepatitis B surface protein, a malarial protein, diphtheria toxoid and sporozoite coat protein of P. falciparum.

12. A method according to claim 6 wherein said carrier is tetanus toxoid or cholera toxin B-chain.

13. A method according to claim 6 wherein said polyvalent vaccine is mixed with an adjuvant selected from the group consisting of alum, detoxified sodium phthalyl derivative of salmonella lipopolysaccharide (SPLPS) and 6-o-dipalmitoyl-glyceryl-succinyl (MDP).

* * * * *

UNITED STATES PATENT AND TRADEMARK OFFICE
CERTIFICATE OF CORRECTION

PATENT NO. : 5,762,931

DATED : June 9, 1998

INVENTOR(S) : Gursaran P. TALWAR, and Debajit K. BISWAS

It is certified that error appears in the above-identified patent and that said Letters Patent is hereby corrected as shown below:

IN THE CLAIMS:
Claim 7, line 3, insert --said-- before "beta".

Signed and Sealed this

First Day of December, 1998

Attest:

BRUCE LEHMAN

*Attesting Officer*   *Commissioner of Patents and Trademarks*